United States Patent [19]

Farley

[11] Patent Number: 4,726,361

[45] Date of Patent: Feb. 23, 1988

[54] METHOD AND APPARATUS FOR CORRECTION OF DEFECTS IN AN EQUINE LEG

[76] Inventor: Michael D. Farley, 1333 Arnoldstown Rd., Burkittsville, Md. 21718

[21] Appl. No.: 819,698

[22] Filed: Jan. 10, 1986

[51] Int. Cl.⁴ .............................................. A61F 5/00
[52] U.S. Cl. ............................... 128/80 B; 128/80 F; 128/88
[58] Field of Search ............... 128/80 C, 80 F, 88, 128/80 R, 77, 80 A, 80 B, 80 J

[56] References Cited

U.S. PATENT DOCUMENTS

| | | | |
|---|---|---|---|
| 308,114 | 11/1884 | Ward | 128/80 R |
| 901,592 | 10/1908 | Clegg | 128/88 |
| 1,007,567 | 10/1911 | Holder | 128/88 |
| 3,669,105 | 6/1972 | Castiglia | 128/80 C |
| 3,805,773 | 4/1974 | Sichau | 128/80 F X |
| 3,826,251 | 7/1974 | Ross | 128/80 F |
| 3,913,302 | 10/1975 | Centers | 128/77 X |
| 4,275,716 | 6/1981 | Scott, Jr. | 128/80 C |
| 4,337,764 | 7/1982 | Lerman | 128/80 F |
| 4,556,053 | 12/1985 | Irons | 128/88 X |

FOREIGN PATENT DOCUMENTS

| | | | |
|---|---|---|---|
| 251960 | 11/1911 | Fed. Rep. of Germany | 128/80 B |
| 2239382 | 2/1974 | Fed. Rep. of Germany | 128/80 F |
| 1153613 | 4/1967 | United Kingdom | 128/80 R |
| 2136294 | 9/1984 | United Kingdom | 128/80 C |

*Primary Examiner*—Clifford D. Crowder
*Attorney, Agent, or Firm*—Berman, Aisenberg & Platt

[57] ABSTRACT

Method and apparatus are disclosed for treatment of various defects in an an animal's leg, particularly the leg of an equine. The apparatus includes a brace attached to the animal's leg at three points. Two pivotal connectors are arranged to be adjacent the knee and ankle joints of a horse's leg, and the spacing between opposed connectors is adequate to accommodate any expected varus or valgus deviation. A pad is provided for engaging a deviated joint and pulling it against a side of the brace to correct the deviation. In accordance with the method of the invention, deviation is corrected by applying the brace to the leg and pulling the deviated joint into its correct position by application of a force with the pad. The pivotal connectors include stop elements to limit the extent of angular motion. A method for treatment of contracture is disclosed whereby a brace is applied to the contracted leg, and the leg is extended in successive steps and prevented from returning to the contracted position by application of the stops. The brace may be applied to either the foreleg or the rear leg of an animal by a simple modification.

6 Claims, 3 Drawing Figures

METHOD AND APPARATUS FOR CORRECTION OF DEFECTS IN AN EQUINE LEG

TECHNICAL FIELD

This invention relates to the art of methods and apparatus for correction of defects in an animal's leg. In particular, the method and apparatus of the invention are preferably used in the correction of defects in the leg of a foal.

BACKGROUND ART

It is common for a foal to be born with one of several defects in its legs. For example, a foal may have a deviation, which is a misalignment of the leg, particularly, the knee joint. If the knee joint is curved outwardly, the deviation is termed a "varus deviation", whereas if the leg is curved inwardly, it is a "valgus deviation." A varus deviation of the knee joint is often accompanied by a valgus deviation of the ankle joint, and vice versa.

It is often that a foal is born with a leg which cannot be extended, and this is termed a "contracture." Other defects or injuries are also common.

These defects become particularly significant when the animal is expensive, such as the offspring of a racehorse. Accordingly, several techniques have been developed in the prior art for correction of these defects.

Perhaps the most popular technique in use is to place the deformed leg in a plaster cast to allow it to grow in the proper manner. This technique is difficult to use and has poor results because the horse considers the plaster cast to be an extremely uncomfortable foreign object and often injures itself trying to escape from the cast.

Other devices are known in the art which are used for various purposes, other than the correction of the specific defects mentioned above. U.S. Pat. No. 3,439,670 (Schuerch) teaches a support for use on a weak or injured leg of a horse. This includes three sections which are attached to the hoof and leg of a horse to provide support. The device fits tightly onto the leg of a horse, and the only restriction to movement of the joints arises from a spring or rod which may be attached between adjacent sections.

U.S. Pat. No. 901,592 (Clegg) teaches a device for preventing the front legs of a horse from hitting each other. This device includes a single joint attached to a horse's foreleg for restricting the movement of the leg.

In addition to devices designed for a horse's leg, it is known to attach braces of various sorts to a human leg. For example, U.S. Pats. Nos. 4,361,142; 4,370,977; and 4,433,679 (Lewis et al., Mauldin et al., and Mauldin et al.) show such braces. These are rarely of any use in treating defects in the leg of an animal such as a horse because of the marked anatomical differences between a leg of a human and a leg of another animal.

SUMMARY OF THE INVENTION

In accordance with the invention, method and apparatus are provided for correction of various defects in an animal's leg. In the preferred embodiment, the apparatus comprises three separate sections of relatively rigid braces with adjacent sections being connected by pivotal elements. The pivotal elements are spaced such that one may be placed approximately adjacent the knee joint of a foal while the second is placed approximately adjacent the ankle joint of the foal. A hoof-engaging element is pivotally attached to the lower end of the lower set of braces, a first attachment band is located between the pivotal elements and a second attachment band is located above the upper pivotal element. The pivotal elements are arranged to provide movement of the three brace sections in a common plane or parallel planes so that the device, in essence, establishes a reference direction for movement of the parts of the leg. The spacing between opposed pivotal elements is large enough to accommodate any expected varus or valgus deviation so that the apparatus may be attached to a deformed leg. In the method of the invention, a pad is used to pull a deviated joint against one of the side braces to urge that joint into proper alignment. By this technique, deviations in both the ankle and knee joints are simultaneously corrected. When applied to a rear leg, misalignment of the tarsal is easily corrected.

Because the apparatus provides pivotal connections, the foal is allowed to walk about, does not view the apparatus as a foreign object, and does not injure itself trying to get away from the apparatus.

Use of the apparatus also relieves pressure on a crushed or deformed knee by properly aligning the weight-bearing carpals. A similar result occurs in the sesamoid bones of the ankle.

The apparatus is also useful for treatment of contractures because the preferred pivotal elements include limiting stops for controlling the angular motions of the brace. A contracture is a deformity where an animal is born with a leg which cannot be extended due to shortened muscles, ligaments, or other dysfunction. The apparatus in accordance with the invention may be used to treat a contracture by attaching the apparatus to the leg and extending the leg by a first amount. The stops on the pivotal connections are placed to prevent the leg from returning to the contracted position, and the leg is subsequently further extended and the stops moved again in succeeding time periods. Ultimately, the leg will be extended to its fullest extent at which time the apparatus may be removed.

It is an object of this invention to provide an apparatus for attachment to an animal leg for treatment of various disorders.

A further object of this invention is to provide an apparatus for attachment to the leg of a horse for correction of valgus or varus deviation of the knee and valgus or varus sesaoid mis-alignment in the ankle joint.

A further object of this invention is to provide an apparatus for attachment to the leg of a horse for treatment of contracture.

Yet another object of this invention is to provide methods for treatment of contracture, deviation, or other dysfunction of an animal leg.

DETAILED DESCRIPTION OF THE DRAWINGS

Figure 1:
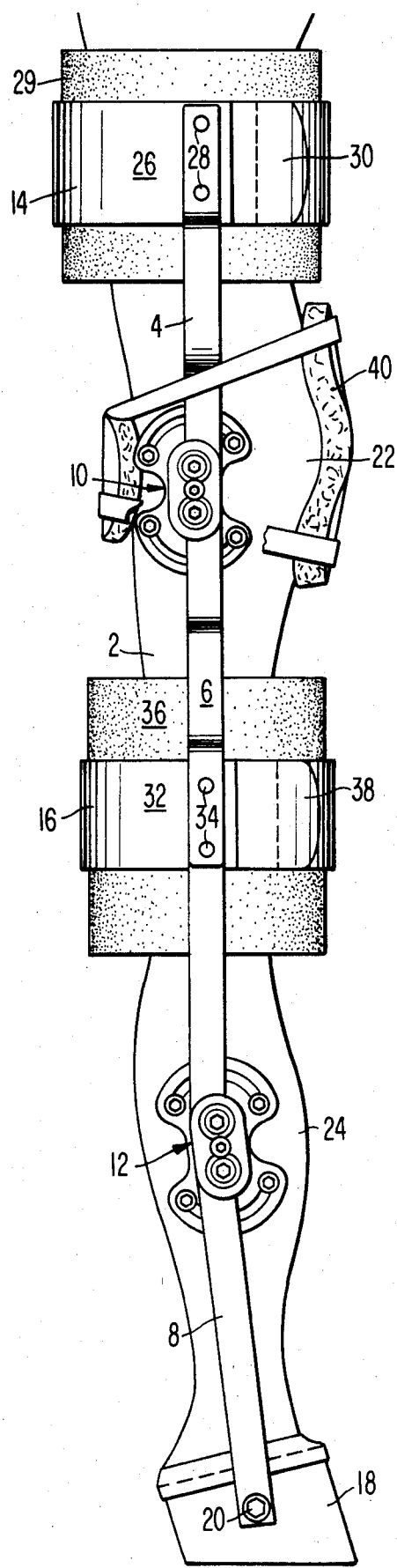
FIG. 1 is a side view of an apparatus in accordance with the invention attached to the leg of a horse.

FIG. 1 is a side view of a preferred form of an apparatus in accordance with the invention attached to a leg 2 of a horse. The apparatus comprises three sections 4, 6 and 8 which are connected by pivotal connectors 10 and 12.

Attachment bands 14 and 16 are secured to sections 4 and 6, respectively, for attaching the apparatus to leg 2. A hoof-engaging element 18 is pivotally attached to section 8 by bolts 20 and receives the hoof of the horse's leg.

Pivotal connector 10 is preferably oriented at a location substantially adjacent the knee 22 of the horse's leg, and pivotal connector 12 is located substantially adjacent the ankle joint 24 of the leg.

Attachment band 14 preferably comprises a rigid semi-cylindrical element 26 which is secured to section 4 by screws, rivets, or the like 28. A pad 29 is secured to semi-cylindrical element 26 and includes a flap 30 for opening pad 29 to allow insertion of leg 2. Attachment band 16 is of a construction similar to that of attachment band 14 and includes semi-cylindrical rigid element 32 which is attached to section 6 by rivets or the like 34. A pad 36 is secured to semi-cylindrical element 32 and is capable of being opened for insertion of the animal's leg and held closed by flap 38.

The apparatus of FIG. 1 is attached to an animal's leg by opening flaps 30 and 38 to allow pads 29 and 36 to be opened. These pads are placed around the animal's leg above and below the knee joint, and the hoof of the animal is placed in the hoof-engaging part 18. The hoof is then preferably secured to the element 18 by taping, or the like, and flaps 30 and 38 are closed to secure the apparatus to the animal's leg.

A significant aspect of the invention is that, because pivotal connectors 10 and 12 are substantially adjacent the knee and ankle joints, respectively, the animal may still move about.

Figure 2:
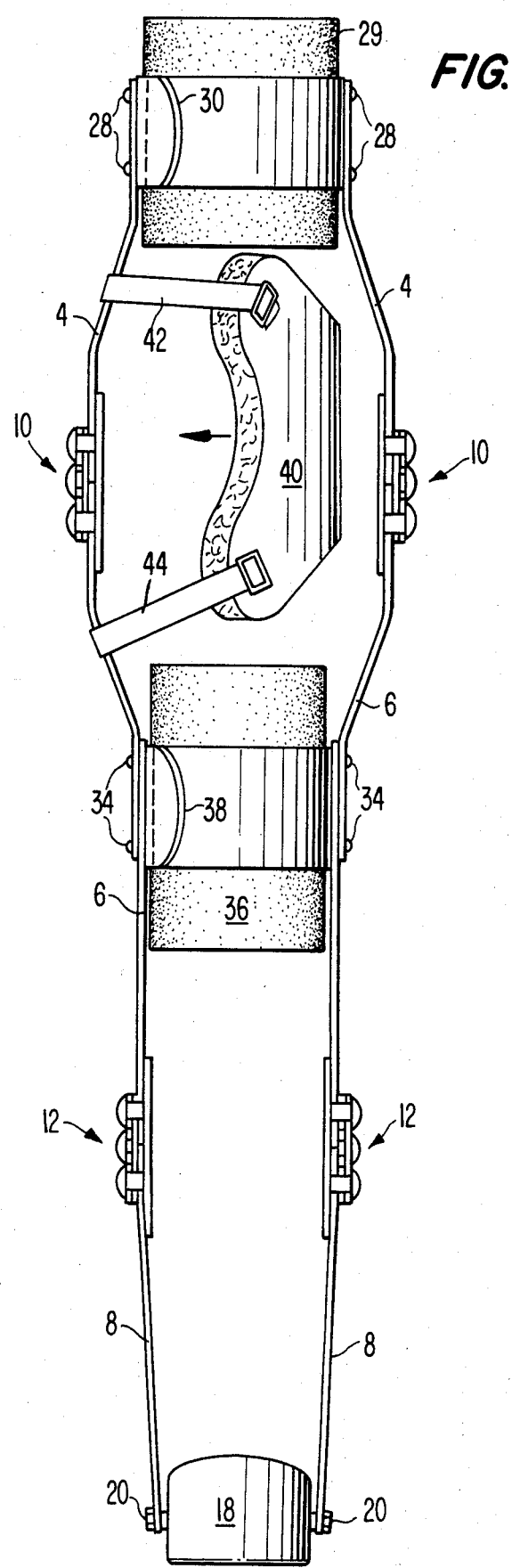
FIG. 2 is a front view of an apparatus in accordance with the invention.

Correction of deviation is accomplished by use of deviation-correction pad 40 shown in FIG. 1, and its use is more clearly described with respect to FIG. 2.

FIG. 2 is a front view of a preferred form of the apparatus in accordance with the invention. The apparatus is substantially symmetrical about a vertical line and sections 4, 6 and 8, and pivotal connectors 10 and 12 as described above with respect to FIG. 1 are duplicated. These elements have been given the same numbers as those in FIG. 1 and perform respectively identical functions.

Use of deviation-correction pad 40 to correct valgus or varus deviation will now be described with respect to FIG. 2. As noted earlier, "deviation" is a curving inwardly or outwardly of the animal's leg, and the cause is a deformity in the bones, muscles, ligaments, or other structure in the leg, particularly at the knee. Deviation of the knee is often accompanied by deviation of the ankle. The apparatus shown in FIG. 2 is useful for correction of deviation because the horizontal distance between opposed pivotal connectors 10 is large enough to accommodate a leg having a substantial amount of valgus or varus deviation. In the preferred embodiment this distance is approximately five and one-half inches. When first attached, the leg having deviation extends from pad 29 into the region between pivotal connectors 10 and through pad 36 with a substantial inward or outward bow in the region between pivotal connectors 10.

In accordance with the inventive method, Applicant has discovered that this deviation can be effectively corrected by attaching deviation-correction pad 40 to the deviated joint and applying a correcting force by pulling the deviated joint in a direction opposite the direction of deviation. This force is applied through straps 42 and 44 which extend from one end of deviation-correction pad 40 around sections 4 and 6 and back to an opposite end of deviation-correction pad 40. The arrow in FIG. 2 illustrates the direction in which a force would be applied by deviation-correction pad 40 to a leg experiencing deviation.

Deviation-correction pad 40 is used to pull the knee into alignment and to hold it there while the leg of the foal matures sufficiently to permit the abnormal joint to grow in the correct manner. In the preferred method, correction is done in a single stage by applying a force to straps 42 and 44 which is sufficient to completetly align the deviated joint and simply to hold it in that position. In certain cases, the correction can be in stages.

Figure 3:
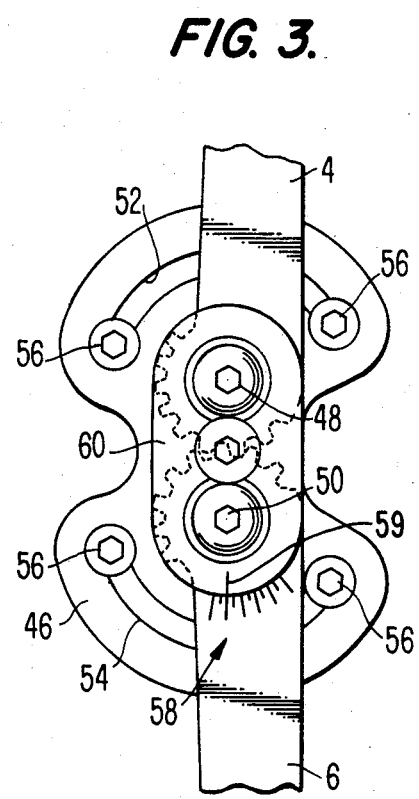
FIG. 3 is a side view of a preferred pivotal connection used in the apparatus of FIGS. 1 and 2.

FIG. 3 shows the preferred pivotal connectors 10, 12, in more detail. It will be appreciated that pivotal connector 12 is designed to permit rotation of section 8 in a counter-clockwise direction when viewed as in FIG. 1 while connector 10 permits rotation of connector 6 in a clockwise direction. Thus, these connectors operate in opposition directions to accommodate the action of an animal's leg.

The embodiments of FIGS. 1 and 2 are for use on a front leg of a foal. The brace may be used on a rear leg by rotating section 8, connector 12 and the part of section 6 below rivets 34 one hundred eighty degrees with respect to the remainder of the brace. The brace can then be used to treat tarsal misalignment in the horse's hock.

With reference to FIG. 3, sections 4 and 6 are attached to a base plate 46 at bolts 48 and 50. The ends of the adjacent sections are geared together as shown in phantom lines to engage each other and pivot about bolts 48 and 50 in unison. Base 46 includes slots 52 and 54, and each slot includes two movable stops 56. These movable stops engage the sides of sections 4 and 6 to limit the angular movement thereof. This feature is useful in Applicant's structure in the treatment of both deviation and contractures. In the treatment of deviation, it sometimes becomes necessary to provide additional support for the animal, and this may be done by limiting the angular movement of sections 4, 6 and 8 to provide a more rigid structure which will give more support to the animal.

The treatment of contractures is accomplished by attaching the apparatus to the animal's leg in the contracted position and pulling the leg outwardly against the force of the abnormally shortened muscles, tendons, or the like. Then stops 56 are moved to prevent retraction of the leg into the contracted position. The leg is pulled further outwardly and the stops 56 repositioned in subsequent time periods until the contracted leg is fully extended. The apparatus is left on the leg until it matures sufficiently to be fully corrected.

Preferably, one of the sections includes a scale such as that shown at 58 which cooperates with an index mark 59 on a cover plate 60 provide an indication of the angular orientation of the sections.

In an actual test of a brace essentially the same as that shown in the drawing figures, an eight-month old filly was treated. The filly experienced sixteen to eighteen degree valgus deviation of the right knee and twenty-two to twenty-four degree varus deviation of the right ankle. The knee was pulled into proper location as determined by x-ray observations and held in that position for a fourteen-day period. This accomplished complete correction of the knee and sixteen to eighteen degree correction of the ankle.

It will be appreciated that unique method and apparatus have been described whereby disorders of an animal's leg may be easily treated. While the preferred apparatus has been described as having three sets of sections 4, 6 and 8, the invention contemplates an apparatus with only sections 4, and 6, or sections 6, and 8. Furthermore, the apparatus contemplates an apparatus which is not symmetrical about a central vertical line thus eliminating the sections and pivotal connectors shown on the right side of the apparatus of FIG. 2.

I claim:

1. Apparatus for correction of defects in a leg of a horse comprising hoof means for securely receiving the hoof of said horse, two first straps pivotally attached to said hoof means, two first pivotal connector means connected to respective ones of said two first straps at a location spaced from said hoof means, two second straps connected to respective ones of said two first pivotal connector means, said first straps being pivotally connected to said second straps for movement in parallel planes by said two first pivotal connector means, two second pivotal connector means connected to respective ones of said second straps at a location spaced from said two first pivotal connector means, two third straps connected to respective ones of said two second pivotal connector means, said second straps being connected to said third straps for rotation in parallel planes about a plurality of axes by said second pivotal connector means, first attachment means secured to at least one of said second straps for attaching said second straps to said leg of a horse at a location below the knee of said leg, second attachment means secured to at least one of said third straps for attaching said third straps to said leg of a horse above the knee of said leg, and force means for engaging the knee of said leg and for applying a force to said knee toward one of said two second pivotal connector means, wherein said two first straps, said two first pivotal connectors, said two second straps, and said two third straps are spaced from each other by a distance adequate to receive said leg therebetween, and said two second pivotal connector means are spaced from each other by a distance adequate to receive therebetween a knee having a valgus or varus deformity.

2. Apparatus according to claim 1 wherein said force means comprises a pad and straps attached to opposite ends of said pad, the length of said straps being adequate to extend from one end of said pad around one of said second pivotal connector means and to the other end of said pad when said pad engages said knee.

3. Apparatus according to claim 2 wherein each of said first and second attachment means comprises a semi-cylindrical rigid element and a strap means for encircling said leg.

4. Apparatus according to claim 1 wherein each of said first and second pivotal connector means includes adjustable stop means for limiting the angular extent of motion between said first and second straps and said second and third straps.

5. A method for treatment of deviation in the leg of a horse comprising attaching an apparatus to said leg, said apparatus comprising hoof means for securely receiving the hoof of said leg, two first straps pivotally attached to said hoof means, two first pivotal connector means connected to respective ones of said two first straps at a location spaced from said hoof means, two second straps connected to respective ones of said two first pivotal connector means, said first straps being pivotally connected to said second straps for rotation in parallel planes by said two first pivotal connector means, two second pivotal connector means connected to respective ones of said second straps at a location spaced from said two first pivotal connector means, two third straps connected to respective ones of said two second pivotal connector means, said second straps being connected for rotation in parallel planes about a plurality of axes to said third straps by said second pivotal connector means, first attachment means secured to at least one of said second straps for attaching said second straps to said leg of a horse at a location below the knee of said leg, second attachment means secured to at least one of said third straps for attaching said third straps to said leg of a horse above the knee of said leg, and force means for engaging the knee of said leg and for applying a force to said knee toward one of said two second pivotal connector means, wherein said two first straps, said two first pivotal connectors, said two second straps, and said two third straps are spaced from each other by a distance adequate to receive said leg therebetween, and said two second pivotal connector means are spaced from each other by a distance adequate to receive therebetween a knee having a valgus or varus deformity, and adjusting said force means to urge said knee in a predetermined direction.

6. A method for treating contracture in the leg of a horse comprising attaching an apparatus to said leg, said apparatus comprising hoof means for securely receiving the hoof of said leg, two first straps pivotally attached to said hoof means, two first pivotal connector means connected to respective ones of said two first straps at a location spaced from said hoof means, two second straps connected to respective ones of said two first pivotal connector means, said first straps being pivotally connected for rotation in parallel planes to said second straps by said two first pivotal connector means, two second pivotal connector means connected to respective ones of said second straps at a location spaced from said two first pivotal connector means, two third straps connected to respective ones of said two second pivotal connector means, said second straps being connected to said third straps for rotation in parallel planes about a plurality of axes by said second pivotal connector means, first attachment means secured to at least one of said second straps for attaching said second straps to said leg of a horse at a location below the knee of said leg, second attachment means secured to at least one of said third straps for attaching said third straps to said leg of a horse above the knee of said leg, and force means for engaging the knee of said leg and for applying a force to said knee toward one of said two second pivotal connector means, wherein said two first straps, said two first pivotal connector means, said two second straps, said two second pivotal connector means, and said two third straps are spaced from each other by a distance adequate to receive said leg therebetween and said first and second pivotal connector means each comprise stop means for limiting the extent of angular movement of said first straps with respect to said second straps and said second straps with respect to said third straps, said method furthur comprising adjusting said stop means to progressively extend said leg.

* * * * *